United States Patent
Wisdom et al.

(10) Patent No.: US 8,975,396 B2
(45) Date of Patent: Mar. 10, 2015

(54) PROCESS FOR THE ASYMMETRIC TRANSFER HYDROGENATION OF KETONES

(75) Inventors: Richard Wisdom, Eppstein (DE); Joerg Jung, Floersheim (DE); Andreas Meudt, Wiesbaden (DE)

(73) Assignee: Euticals GmbH, Frankfurt am Main (DE)

( * ) Notice: Subject to any disclaimer, the term of this patent is extended or adjusted under 35 U.S.C. 154(b) by 179 days.

(21) Appl. No.: 13/701,580

(22) PCT Filed: Apr. 14, 2011

(86) PCT No.: PCT/EP2011/001887
§ 371 (c)(1),
(2), (4) Date: Jan. 9, 2013

(87) PCT Pub. No.: WO2011/131315
PCT Pub. Date: Oct. 27, 2011

(65) Prior Publication Data
US 2013/0123490 A1 May 16, 2013

(30) Foreign Application Priority Data

Apr. 23, 2010 (EP) .................................... 10004348

(51) Int. Cl.
*C07D 223/28* (2006.01)
(52) U.S. Cl.
CPC ........... *C07D 223/28* (2013.01); *C07B 2200/07* (2013.01)
USPC ........................................................ 540/589

(58) Field of Classification Search
CPC ...................................................... C07D 223/22
USPC .......................................................... 540/589
See application file for complete search history.

(56) References Cited

U.S. PATENT DOCUMENTS 8,288,532 B2 * 10/2012 Learmonth et al. ........... 540/589
2009/0062573 A1 3/2009 Miki et al.

FOREIGN PATENT DOCUMENTS

| EP | 0 751 129 A1 | 1/1997 |
| EP | 1 385 826 | 11/2002 |
| EP | 1 477 480 A1 | 11/2004 |
| WO | WO 2004/031155 A1 | 4/2004 |
| WO | WO 2007/012793 A1 | 2/2007 |

OTHER PUBLICATIONS

Benes, J. et al., "Anticonvulsant and Sodium Channel-Blocking Properties of Novel 10,11-Dihydro-5*H*-dibenz[b,*f*]azepine-5-carboxamide Derivatives" *J. Med. Chem.*, 42 (1999) pp. 2582-2587.

* cited by examiner

*Primary Examiner* — Yong Chu
(74) *Attorney, Agent, or Firm* — ProPat, L.L.C.

(57) ABSTRACT

The invention relates to a process for the asymmetric transfer hydrogenation of a ketone substrate to produce as chiral secondary alcohol with an ee of greater than 85% in which an enantio-enriched chiral catalyst containing ruthenium or rhodium is used with a hydrogen donor and in which an anion exchange resin is used as a base.

15 Claims, No Drawings

PROCESS FOR THE ASYMMETRIC TRANSFER HYDROGENATION OF KETONES

Eslicarbazepine acetate is a 'third generation' single enantiomer antiepileptic drug which has recently gained European Marketing Approval (April 2009) for use as an 'add-on' treatment with other anti-epileptic medicines. Eslicarbazepine acetate is a pro-drug and it is converted in the body to the active compound Eslicarbazepine. Eslicarbazepine is believed to act in the body by blocking voltage-gated sodium channels limiting sodium entry to nerve cells. This results in reduced nerve cell activity in the brain leading to a reduction in the intensity and numbers of seizures.

The chemical systematic name for Eslicarbazepine acetate is (S)-10-acetoxy-10,11-dihydro-5H-dibenz[b,f]azepine-5-carboxamide. It was initially described in EP0751129 which gives a description of its potential for therapeutic use.

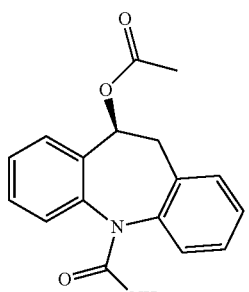

Eslicarbazepine acetate-
(S)-10-acetoxy-10,11-dihydro-5H-dibenz[b,f]azepine-5-carboxamide Work by J Benes et al J. Medicinal Chemistry 42 2582-87 (1999) described a route for synthesis of the single enantiomer product via chemical reduction of 10-oxo-10,11-dihydro-5H-dibenz[b,f]azepine-5-carboxamide (oxcarbazepine) followed by resolution of the resulting racemic alcohol to give the (S) enantiomer and then acetylation. Resolution of the alcohol was achieved by the formation of diastereoisomeric menthoxyacetate esters followed by crystallisation and release of the enantiomerically pure (S)-10,11-dihydro-10-hydroxy-5H-dibenz[b,f]azepine-5-carboxamide (eslicarbazepine, (S)-MHD). This route suffers from a high price for the resolving agent and a large number of steps. An alternative resolution is described in EP1385826. This details chemical reduction of the ketone with sodium borohydride to form racemic-10-hydroxy-10,11-dihydro-5H-dibenz[bf]azepine-5-carboxamide. This is also resolved and then acetylated. The resolution is achieved by reaction of the alcohol with diacetyl tartartic acid anhydride, carrying out crystallisation until a diasteroisomer of the required diasteromeric purity is obtained, after which the tartaric acid and acetic acid are released by saponification with sodium hydroxide. Following isolation of the eslicarbazepine and acetylation, the required eslicarbazepine acetate is obtained. In order to minimise material loss, the undesired (R) enantiomer can be recovered from the mother liquors of the resolution, racemised and recycled for further resolution. A suitable procedure for this racemisation has been provided in EP1477480. Compared to the report by J. Benes et al. (1999), this uses cheaper and more readily available resolving agents, however the route still suffers from too many steps and would be costly to perform.

WO2004031155 describes a potentially more interesting route to the single enantiomer eslicarbazepine intermediate. In this application, asymmetric transfer hydrogenation of oxcarbazepine is used in place of sodium borohydride to directly produce the required single enantiomer with high enantiomeric purity. The catalyst used is one well described for use in such asymmetric hydrogenations—a ruthenium catalyst in combination with a chiral diamine sulfonic acid derivative ligand, eg chloro{[(1S,2S)-(+)-2-amino-1,2-diphenylethyl](4-toluenesulfonyl)amido}(p-cymene) ruthenium(II)-(RuCl[(S,S)-Ts-DPEN](p-cymene)). In this application the reaction is carried out using formic acid as a source of hydrogen and triethylamine as a base. Although highly enantiopure eslicarbazepine is obtained, catalyst usage is very high at approximately 1 mol-% and concentrations of reactants are low. Such a process would be prohibitively expensive at scale. WO2007012793 also describes asymmetric transfer hydrogenation of oxcarbazepine to produce eslicarbazepine. This was then acetylated using acetic anhydride to produce the required eslicarbazepine acetate. Although a similar type of catalyst to that described in WO2004031155 is used, the conditions of the reaction are altered so that the pH is maintained throughout the reaction at 7.40-7.45 by the continuous titration of the reaction with a formic acid solution. In this way a molar catalyst to substrate ratio of 1:1000, or even greater than 1:3000, was achieved. At these low catalyst loadings, the potential for carry through of residual ruthenium to final product is reduced and catalyst cost becomes much less significant. Although a considerable improvement on prior art, there is still a need for a robust process that doesn't require continuous monitoring and pH control within such a narrow range, which makes the process difficult to run at a larger scale with well reproducible results (mandatory for pharmaceutical applications).

It has surprisingly been found that high conversions with good ee (enantiomeric excess) can be obtained by using a weak anionic ion exchange resin in place of triethylamine or other tertiary amines as base. A weak anion exchange resin is a highly porous support matrix, usually in the form of beads, on the surface of which are found weakly basic functional groups. These groups are tertiary (ternary) or potentially secondary amines and allow for the exchange of anionic species. Use of such anionic exchange resins enables a very good rate of asymmetric transfer hydrogenation at low catalyst loading. Additionally, at the completion of the reaction the base and acid can be removed from the reaction mixture by a simple filtration, which facilitates the work-up of the reaction. Precise control of pH is not required and it is found that good performance can be obtained between pH 5 and 8. This allows much greater flexibility in operation and less dependence on exact pH measurement in a solution of refluxing solvent.

Additionally, it has very surprisingly been found that it is possible, with an ion exchange resin, to operate the transfer hydrogenation at relatively high starting oxcarbazepine concentrations with a single charge of formic acid at the start of the reaction. It is not necessary to continuously, or semi-continuously, add formic acid as the reaction proceeds. The consumption of formic acid during the hydrogenation, and transfer of the reducing equivalents during the catalytic cycle to the starting ketone is so efficient that the reaction can be run with less than 2 mole equivalents of hydrogen per mole of oxcarbazepine. This results in the formation of less hydrogen as a by-product leading to a safer reaction. For comparison in WO2007012793A1, Example 1, 3,7 mol eq formic acid are required for good conversion of the oxcarbazepine. Using a weak anion exchange resin as a base, greater than 97% conversion of starting oxcarbazepine can be achieved when only 1,5 mole equivalents of formic acid are added at the start of the reaction. No further formic acid additions are required, and there is consequently no need to monitor the pH of the reaction. Compared to the prior art, this is a considerable improvement leading to a superior reaction which is simpler to control.

Further the conversion is quicker if suitable ion exchangers are used compared to the reaction using tertiary amine bases. Although the reason for this considerable rate increase is not completely clear, good explanations for this important effect are either the scavenging of catalysts poisons by the resin or a specific interaction of the catalyst with the resin surface. The higher reaction rates potentially also allow for a reduction of the used catalyst amount, which has a huge influence on economics because the catalyst is still a major costs driver in this reaction although the activity is very high under the conditions described.

The route to the desired eslicarbazepine acetate according to the present invention is shown below.

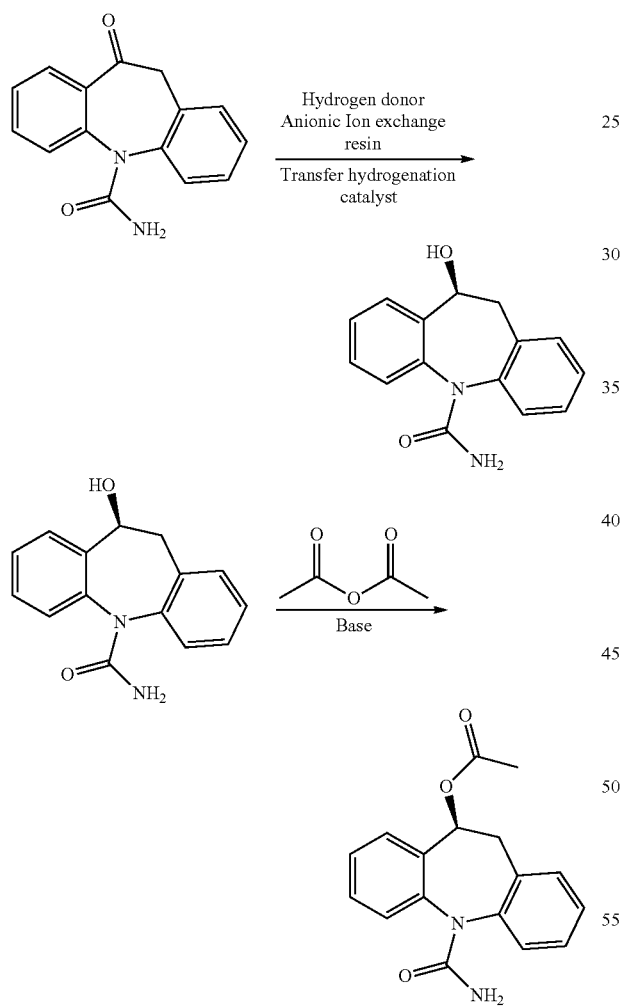

The reduction is carried out using a suitable chiral catalyst. These catalysts have the general formula:

RuX(L1)(L2), where

X is a halogen, typically a chlorine atom,

L1 is a ligand such as p-cymene or mesitylene or toluene or p-xylene or m-xylene or other C6 to C14 arene or C5 to C12 heteroarene compound, and L2 is a chiral diamine ligand as shown below:

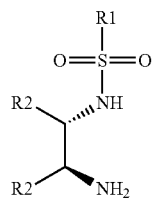

Ligand L2 where

R1, R2 are similar or different C6 to C14 aryl or C5 to C12 heteroaryl rings or C1 to C12 alkyl groups, optionally substituted with one or more C1 to C12 alkyl, halogen or C1 to C12 alkoxy groups.

In a preferred embodiment of the invention R2 in the Ligand L2 is phenyl, 2-methylphenyl, 3-methylphenyl, 4-methylphenyl or 4-methoxyphenyl and —SO$_2$—R1 is p-tosyl, methanesulfonyl, 4-benzenesulfonyl, or pentafluorophenylsulfonyl. Specific examples of the most preferred catalysts are: chloro{[(1S,2S)-(−)-2-amino-1,2-diphenylethyl] (pentafluorophenylsulfonyl) amido}(p-cymene) ruthenium(II) (also known as (RuCl[(S,S)-Fs-DPEN](p-cymene)) or chloro{[(1S,2S)-(+)-2-amino-1,2-diphenylethyl](methanesulfonyl)amido}(p-cymene) ruthenium(II) (known as RuCl [(S,S)-Ms-DPEN](p-cymene)), or chloro{[(1S,2S)-(+)-2-amino-1,2-diphenylethyl](4-toluenesulfonyl)amido}(p-cymene) ruthenium(II) (known as RuCl [(S,S)-Ts-DPEN](p-cymene)).

Alternatively a catalyst of the following closely related structure may be used.

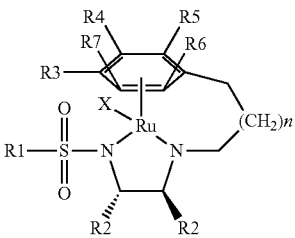

In which n is an integer, either 0 or 1 or 2 or 3 or 4 or 5 or 6

X is a halogen, typically a chlorine atom and

R1 and R2 are are similar or different C6 to C14 aryl or C5 to C12 heteroaryl rings or C1 to C12 alkyl groups, optionally substituted with one or more C1 to C12 alkyl, halogen or C1 to C12 alkoxy groups, and R3, R4, R5, R6 and R7 are similar or different and are hydrogen or C1 to C3 alkyl groups.

In the preferred embodiment of the reaction X is a chlorine atom, n is 1, R1 is 4-methylphenyl, R2 is phenyl and R3, R4, R5, R6 and R7 are hydrogen—[N-[3-((1,2,3,4,5,6-η)-phenyl)-propyl]-(1S,2S)-1,2-diphenyl-1-(4-methylbenzenesulphonyl-amidato(κN')-ethyl-2-amino-κN]-ruthenium(II) chloride—(also known as RuCl [(S,S)-teth-TsDPEN]).

Suitable catalysts may be prepared in the laboratory using published methods or are available commercially from a suitable catalyst supply company.

The source of hydrogen in the transfer hydrogenation can be any hydrogen donor known in the literature as suitable in transfer hydrogenations, i.e. formic acid or a salt or derivative of formic acid, cyclohexene or 1-methylcyclohexane. In the most preferred embodiment, formic acid or a salt thereof is used as hydrogen donor.

The selection of base is important as it is found that different bases do not necessary give a good performance. Tertiary amines, such as triethylamine, are often described for such reactions, however it has been claimed in WO2007012793A1, that it is necessary to maintain the pH of the reaction within a narrow range of pH 6.5 to 8.0 to obtain good reaction. Indeed within the examples provided in this application, the pH is maintained within an extremely narrow range of pH 7.40-7.45 by constant titration with formic acid. Thus as the formic acid is consumed to produce carbon dioxide plus the hydrogen which is required for the reduction (or also hydrogen gas by-product), the pH is expected to increase. Addition of extra formic acid is required to maintain the pH and to provide more reducing power to push the reaction to completion.

A weak anion exchange resin has been surprisingly found to work well as a base. In such a case the base can readily be removed from the reaction at completion.

Ion exchange resins suitable for the invention are basic ion exchange resins, i.e. ion exchange resin with non quarternary nitrogen atom present in the polymer. In a preferred embodiment of the invention, the ion exchange is a copolymer of a functionalised acrylate, other suitable monomers, and optionally cross-linkers. In the most preferred embodiment of the invention, the functionalised acrylate is N,N-dimethylaminopropylacrylamide, the additional monomers are di(ethylene glycol) divinyl ether and divinylbenzene. A technical version of this resin is available from Rohm and Haas (now Dow) with the trade name Amberlite® IRA-67 (CAS No 65899-87-8), which is a tertiary amine on an acrylate polymer porous resin. Other tertiary weak anionic exchange resins can also be considered suitable for this application.

As an alternative to the use of an anion exchange resin it has surprisingly been found that a quaternary amine such as tetramethylammonium hydroxide works well as a base. In such a case a wider range of pH is tolerated throughout the reaction and close continuous control is therefore not required, allowing for a more robust process. This can be achieved without resorting to high catalyst loadings which have a detrimental effect on process economics and potentially on product quality. Such bases have not been previously considered for this reaction. Tetramethylammonium hydroxide is commercially available as a 25% w/w solution in water from SigmaAldrich (cat #331635). It will be understood that other quaternary bases or alternative base concentrations or alternative solvents to water may also be considered suitable for this application.

The asymmetric transfer hydrogenation reaction is carried out in a suitable solvent at elevated temperatures. Ethyl acetate at reflux has been found to work well in this reaction, though other solvents may also be considered, particularly esters (i.e. butylacetate, propylacetate, isopropylacetate). Water is preferably added. The base, either the ion exchange resin or the quaternary amine, and the formic acid may be added separately. The ion exchange resin may be optionally pre-treated to remove trace impurities from the manufacturing process. Alternatively ion exchange resin from a previous reaction may be isolated and re-cycled. The quaternary amine may be supplied as a solution in water or other suitable solvent. The catalyst may be dissolved in a suitable solvent such as dimethylformamide. The transfer hydrogenation is carried out until a conversion of >95%, more preferably >98% is reached with extra formic acid added if, or as required.

At completion of reaction, the formed (S)-(+)-10-hydroxy-10,11-dihydro-5H-dibenz[b,f]azepine-5-carboxamide (eslicarbazepine) may be isolated by filtration of the resin (where used), cooling to room temperature, or more preferably to <8° C., optionally with the addition of a co-solvent such as methyl tert-butyl ether (MTBE) in which the alcohol product has very poor solubility. The precipitated product may then be readily isolated by filtration and washed with a suitable solvent.

Formation of the desired (S)-10-acetoxy-10,11-dihydro-5H-dibenz[b,f]azepine-5-carboxamide from (S)-(+)- 10-hydroxy-10,11-dihydro-5H-dibenz/b, f/azepine-5-carboxamide is carried out using standard acetylating procedures. Thus, reaction of eslicarbazepine with acetic anhydride with a base such as triethylamine or pyridine and preferably a catalytic amount of dimethylaminopyridine and optionally a suitable solvent such as dichloromethane yields (S)-10-acetoxy-10,11-dihydro-5H-dibenz[b,f]azepine-5-carboxamide. The product may be isolated by optionally washing with water, followed by crystallisation from a suitable solvent. Crystallisation affords not only increases in chemical purity, but is also able to give an improvement in optical purity of the product. Isopropanol has been found to be a good solvent for crystallisation; however other solvents may readily be tested and selected using standard procedures.

Example 1

In a 1 L flask with overhead stirrer, reflux condenser, thermometer, dropping funnel and under nitrogen were combined: 64 g oxcarbazepine, 480 ml of ethyl acetate, 112 g IRA-67 tertiary ion exchange resin (SigmaAldrich, cat 476633), 40 ml water and 11.7 g formic acid. 120 mg RuCl [(S,S)-Ts-DPEN](p-cymene) (Takasago) was dissolved in 40 ml dimethylformamide and added to the reaction. The reaction was heated in an oil bath to reflux. The pH was checked approximately every 30-90 minutes and formic acid added as required from the dropping funnel to about pH 5.4.

In this way the pH was maintained between 5.4 and 7. Overnight the reaction was left without formic acid addition (in the morning a pH of 7.3 was reached). After 24 hours the conversion was 99% (HPLC area % at 210 nm). The product was isolated by filtering off the ion exchange resin and washing the resin with 50 ml ethyl acetate. The organic phase was then washed with 20 ml water, and the product precipitated by addition of 200 ml tert-butyl methyl ether (MTBE) and cooling to 0-4° C. on ice. After filtration and washing with MTBE, the product was dried to give eslicarbazepine (74% yield) with a purity (HPLC a/a %, 210 nm) of 99.4% and ee of 98.8%.

Example 2

42 g IRA-67 tertiary ion exchange resin (SigmaAldrich, cat 476633) was washed by refluxing in a mixture of 350 ml ethyl acetate plus 50 ml water for 15 minutes, and then filtering.

In a 500 ml flask with overhead stirrer, reflux condenser, thermometer and under nitrogen were combined: 24 g oxcarbazepine, 180 ml of ethyl acetate, 42 g IRA-67 tertiary ion exchange resin (washed as described above), 9 ml water and 4.4 g formic acid. 52 mg RuCl [(S,S)-Ts-DPEN](p-cymene) was dissolved in 4 ml dimethylformamide and added to the reaction. Using an oil bath, the reaction was heated to reflux. The pH was checked approximately every 30-60 minutes and formic acid added as required to about pH 5.4. In this way the pH was maintained between 5.4 and 7. Overnight the reaction was left without formic acid addition. After 26 hours the conversion was 98% (HPLC area % at 210 nm). The product was isolated by filtering off the ion exchange resin and washing the resin with 15 ml ethyl acetate. The combined organic phase was then cooled to 0-4° C. on ice. After filtration and washing with ethyl acetate, the product was dried to give eslicarbazepine (yield 81%) with a purity (HPLC a/a %, 210 nm) of 98.8% and ee of 98.1%.

Example 3

The product from Example 1 was acetylated and isolated to give eslicarbazepine acetate. In a 500 ml flask with overhead stirrer, reflux condenser, thermometer and under nitrogen were added 25.4 g of eslicarbazepine (Example 1), 153 ml dichloromethane, 12.8 g acetic anhydride, 13.6 g triethylamine and 51 mg dimethylamino pyridine. The reaction was brought to reflux (internal temperature 45° C.) for 2 hours, at which point the reaction was complete (0.3% starting eslicarbazepine remaining). The product was isolated by washing 2 times with 76 ml water, exchanging the dichloromethane to isopropanol and crystallising from isopropanol by warming to ensure complete dissolution of the eslicarbazepine acetate and slowly cooling over several hours to room temperature. The product was then filtered and washed 2 times with isopropanol. HPLC purity of product was >99.9% a/a, residual ruthenium content was <2 ppm and ee was 99.8%.

Example 4

In a 250 ml flask with overhead stirrer, reflux condenser and under nitrogen were combined: 16 g oxcarbazepine (63 mmol, 1 mol eq), 120 ml of ethyl acetate, 35 g IRA-67 tertiary ion exchange resin (SigmaAldrich, cat 476633), 10 ml water and 4.4 g formic acid (96 mmol, 1.5 mol eq). 35 mg RuCl [(S,S)-Ts-DPEN](p-cymene) (SigmaAldrich #703915) was dissolved in 10 ml dimethylformamide and added to the reactor. The reaction was heated in an oil bath to reflux. After 29 hours, without any further formic acid addition, the conversion had reached 98,4%. Product was isolated by filtering off the resin and washing with a 20 ml ethyl acetate. The combined organic phases were then washed with 10 ml water which was separated off. After cooling in the fridge, the product was filtered off and washed twice with 15 ml ethyl acetate. The isolated product had an ee of 98%. After acetylation and crystallisation using a similar method to that described in Example 3, eslicarbazepine acetate was isolated with an ee of 99.8% and product purity of 99.9% (HPLC area %, 210 nm).

Example 5

In a 500 ml flask with overhead stirrer, reflux condenser, thermometer and under nitrogen were combined: 16 g oxcarbazepine, 120 ml of ethyl acetate, 28 g IRA-67 tertiary ion exchange resin (washed as described above), 10 ml water and 2.9 g formic acid. 52 mg chloro{[(1S,2S)-(+)-2-amino-1,2-diphenylethyl](methane-sulfonyl)amido}(p-cymene) ruthenium(II) (RuCl [(S,S)-Ms-DPEN](p-cymene)) was dissolved in 10 ml dimethylformamide and added to the reaction. Using an oil bath, the reaction was heated to reflux. The pH was checked approximately every 30-60 minutes and formic acid added as required to about pH 5.4. In this way the pH was maintained between 5.4 and 8. Overnight the reaction was left without formic acid addition. After 24 hours the conversion was >99% (HPLC area % at 210 nm). The product was isolated by filtering off the ion exchange resin and washing the resin with 15 ml ethyl acetate. The combined organic phase was washed with 5 ml water, then cooled to 0-4° C. on ice. After filtration and washing with ethyl acetate, the product was dried to give eslicarbazepine with a purity (HPLC a/a %, 210 nm) of >99% and ee of 98%.

A similar reaction was carried out using [N-[3-((1,2,3,4,5,6-η)-phenyl)-propyl]-(1S,2S)-1,2-diphenyl-1-(4-methyl-benzenesulphonylamidato(κN')-ethyl-2-amino-κN]-ruthenium(II) chloride (RuCl [(S,S)-teth-TsDPEN]) as a catalyst (Johnson Matthey product C1-310). After 30 hours, conversion was 83%, ee was 86%.

Although the enantiomeric purity with RuCl [(S,S)-teth-TsDPEN] as a catalyst is lower than RuCl [(S,S)-Ms-DPEN](p-cymene) or RuCl [(S,S)-Ts-DPEN](p-cymene), it has been shown that eslicarbazepine acetate with an ee of 85% may be successfully crystallised from a suitable solvent such as isopropanol to yield eslicarbazepine acetate with an ee of 99% in a single crystallisation.

Example 6

In a 250 ml flask with thermometer, reflux condenser, stirrer and under nitrogen was added 8 g oxcarbazepine, 60 ml of ethyl acetate, 18 ml tetramethylammonium hydroxide (25% solution in water), 2 ml formic acid and 5 ml water. 21 mg RuCl [(S,S)-Ts-DPEN](p-cymene) (SigmaAldrich 703915) was dissolved in 5 ml dimethylformamide and added to the reaction. The reaction was heated in an oil bath to reflux. The pH was checked approximately every 30 to 60 minutes and formic acid added as required to about pH 5. In this way the pH was maintained between 5 and 9. After 7 hours the conversion was 80% and after overnight reaction without further formic acid addition a conversion (HPLC area % at 210 nm) of 96% was obtained with a product ee of 97.1% of (S)-(+)-10-hydroxy-10,11-dihydro-5H-dibenz[b,f]azepine-5-carboxamide (pH 8.5). The reaction was cooled on ice for 4 hours with stirring, filtered and washed 2 times with 20 ml methyl tert-butyl ether (MTBE) to yield 7.5 g alcohol after drying with a purity of 99,3% (HPLC a/a %).

Example 7

In a 1 L flask with overhead stirrer, reflux condenser and under nitrogen were combined: 80 g oxcarbazepine, 600 ml of ethyl acetate, 180 ml tetramethylammonium hydroxide (25% solution in water, Sigma Aldrich, cat #331635), and 22 ml formic acid. 150 mg RuCl [(S,S)-Fs-DPEN](p-cymene) (Strem cat 44-0157) was dissolved in 50 ml dimethylformamide and added to the reaction. The reaction was heated in an oil bath to reflux. The pH was checked approximately every 30-120 minutes and formic acid added as required to bring the between pH 5 and 6 (no formic acid added overnight). After 30 hours the conversion was 64% and a further charge of 100 mg catalyst was added. After 48 hours, the reaction conversion was 96%, ee 97.1%.

The invention claimed is:

1. A process for the asymmetric transfer hydrogenation of a ketone substrate to produce a chiral secondary alcohol with an ee of greater than 85% in which an enantio-enriched chiral catalyst containing ruthenium or rhodium is used with a hydrogen donor and in which a weak anion exchange resin is used as a base,
wherein the starting ketone is 10-oxo-10,11-dihydro-5H-dibenz[b,f]azepine-5-carboxamide and the product alcohol is (S)-10,11-dihydro-10-hydroxy-5H-dibenz[b,f]azepine-5-carboxamide.

2. A process tbr the asymmetric transfer hydrogenation of a ketone substrate to produce a chiral secondary alcohol with an ee of greater than 85% in which an enantio-enriched chiral catalyst having an enantiomeric excess greater than 90% is used with a hydrogen donor and in which a weak anion exchange resin is used as a base, where the catalyst: either has the formula RuX(L1)(L2), where X is a halogen.

L1 is p-cymene or mesitylene or toluene or p-xylene or m-xylene or other C6 to C14 arene or C5 to C12 heteroarene compound, and L2 is the chiral diamine ligand

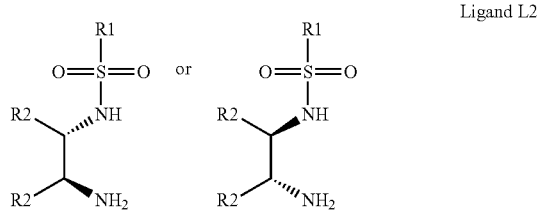

Ligand L2 where

R1, R2 are similar or different C6 to C14 aryl or C5 to C12 heteroaryl rings or C1 to C12 alkyl groups, optionally substituted with one or more C1 to C12 alkyl, halogen or C1 to C12 alkoxy groups or the catalyst has the structure

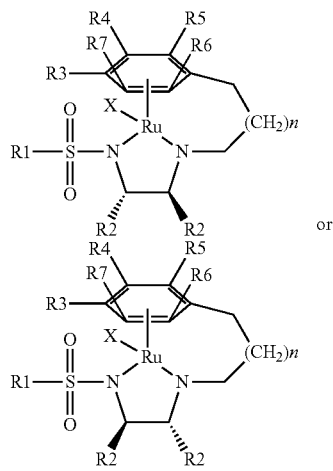

where X, R1 and R2 are as defined above and n is an integer between 0 and 6 and R3, R4, R5, R6 and R7 are similar or different hydrogen or C1 to C3 alkyl groups.

3. A process according to claim 2 in which the starting ketone is 10-oxo-10,11-dihydro-5H-dibenz[b,f]azepine-5-carboxamide and the product alcohol is (S)-10,11-dihydro-10-hydroxy-5H-dibenz[b,f]azepine-5-carboxamide.

4. A process according to claim 1 in which formic acid or a salt of formic acid is used as the hydrogen donor.

5. A process according to claim 1 in which the weak anion exchange resin is a porous support matrix on a surface of which are found weakly basic functional groups selected from tertiary or secondary amines.

6. A process according to claim 5 in which the weak anion exchange resin used is of a porous acrylate gel structure.

7. A process according to claim 5 in which the weak anion exchange resin used is a copolymer of N,N-dimethylaminopropylacrylarmide, a vinyl ether derivative and another monomer.

8. A process according to claim 7 in which the weak anion exchange resin used is a copolymer of N,N-dimethylaminopropylacrylamide, di(ethylene glycol) divinyl ether and divinylbenzene.

9. A process according to claim 3 in which the formed (S)-10,11-dihydro-10-hydroxy-5H-dibenz[b,f]azepine-5-carboxamide (eslicarbazepine) is of ee greater than 96%.

10. A process according to claim 3 in which the formed S)-10,11-dihydro-10-hydroxy-5H-dibenz[b,f]azepine-5-carboxamide is isolated and then acetylated to produce (S)-10-acetoxy-10,11-dihydro-5H-dibenz[b,f]azepine-5-carboxamide (eslicarbazepine acetate).

11. A process the asymmetric transfer hydrogenation of a ketone substrate to produce a chiral secondary alcohol with an ee of greater than 85% in which an enantio-enriched chiral catalyst containing ruthenium or rhodium is used and in which formic acid is added as a source of hydrogen and a quaternary amine is used as a base, wherein the starting ketone is 10-oxo-10,11-dihydro-5-H-dibenz[b,f]azepine-5-carboxamide and the product alcohol is (S)-10,11-dihydro-10-hydroxy-5H-dibenz[b,f]azepine-5-carboxamide (eslicarbazepine).

12. A process for the asymmetric transfer hydrogenation of a ketone substrate to produce a chiral secondary alcohol with an ee of greater than 85% in which an enantio-enriched chiral catalyst having an enantiomeric excess greater than 90% is used with a hydrogen donor and in which a quarternary amine is used as a base, where the catalyst:

either has the formula RuX(L1)(L2), where

X is a halogen,

L1 is p-cymene or mesitylene or toluene or p-xylene or m-xylene or other C6 to C14 arene or C5 to C12 heteroarene compound, and L2 is the chiral diamine ligand

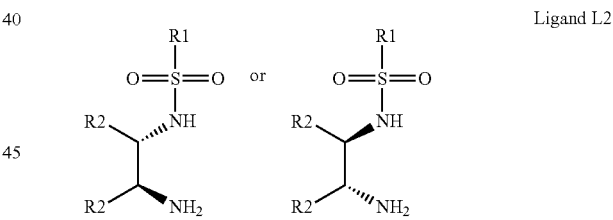

Ligand L2 where

R1, R2 are similar or different C6 to C14 aryl or C5 to C 12 heteroaryl rings or C1 to C 12 alkyl groups, optionally substituted with one or more C1 to C12 alkyl, halogen or C1 to C12 alkoxy groups or the catalyst has the structure

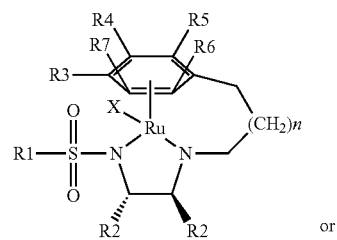

or

-continued

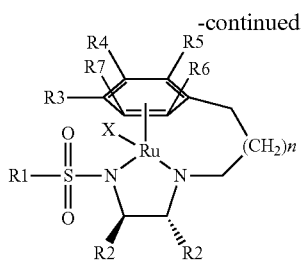

where X, R1 and R2 are as defined above and n is an integer between 0 and 6 and R3, R4, R5, R6 and R7 are similar or different hydrogen or C1 to C3 alkyl groups.

13. A process according to claim 12 in which the starting ketone is 10-oxo-10,11-dihydro-5H-dibenz[b,f]azepine-5-carboxamide and the product alcohol is (S)-10,11-dihydro-10-hydroxy-5H-dibenz[b,f]azepine-5-carboxamide (eslicarbazepine).

14. A process according to claim 12 in which the quaternary amine is tetramethylammonium hydroxide.

15. A process according to claim 13 in which the formed (S)-10,11-dihydro-10-hydroxy-5H-dibenz[b,f]azepine-5-carboxamide is isolated and then acetylated to produce (S)-10-acetoxy-10,11-dihydro-5H-dibenz[b,f]azepine-5carboxamide.

* * * * *

UNITED STATES PATENT AND TRADEMARK OFFICE
CERTIFICATE OF CORRECTION

| | | |
|---|---|---|
| PATENT NO. | : 8,975,396 B2 | Page 1 of 1 |
| APPLICATION NO. | : 13/701580 | |
| DATED | : March 10, 2015 | |
| INVENTOR(S) | : Richard Wisdom, Joerg Jung and Andreas Meudt | |

It is certified that error appears in the above-identified patent and that said Letters Patent is hereby corrected as shown below:

In the Claims:

In Column 9, line 66, Claim 7    delete "propylacrylarmide" insert -- propylacrylamide --
In Column 10, line 20, Claim 11  delete "5-H-" insert -- 5H- --
In Column 11, line 25, Claim 15  delete "5car-" insert -- 5-car- --

Signed and Sealed this
Thirtieth Day of June, 2015

Michelle K. Lee
*Director of the United States Patent and Trademark Office*